United States Patent [19]
Hardison

[11] Patent Number: 5,209,743
[45] Date of Patent: May 11, 1993

[54] REUSABLE DIAPER AND THE LIKE

[75] Inventor: Christine Hardison, Somerset, N.J.

[73] Assignee: General Health Care Corp., Piscataway, N.J.

[21] Appl. No.: 749,198

[22] Filed: Aug. 23, 1991

[51] Int. Cl.⁵ ............... A61F 13/15; A61F 13/20; A41B 9/00; A41B 9/04
[52] U.S. Cl. .................. 604/391; 604/358; 604/386; 604/385.1; 604/385.2; 604/390; 2/111; 2/406; 2/408; 2/DIG. 6; 2/DIG. 7
[58] Field of Search ............ 2/111, 406, 408, DIG. 7, 2/DIG. 6; 604/391, 385.1, 385.2, 378, 386, 390, 358

[56] References Cited

U.S. PATENT DOCUMENTS

| | | | |
|---|---|---|---|
| 3,653,381 | 4/1972 | Warnken | 604/391 |
| 4,617,022 | 10/1986 | Pigneul et al. | 604/391 |
| 4,718,901 | 1/1988 | Singheimer | 604/385.2 |

FOREIGN PATENT DOCUMENTS

| | | | |
|---|---|---|---|
| 0236324 | 7/1960 | Australia | 604/378 |
| 9007313 | 7/1990 | World Int. Prop. O. | 604/385.2 |

Primary Examiner—Randall L. Green
Assistant Examiner—Paul Zuttarelli
Attorney, Agent, or Firm—Lackenbach, Siegel, Marzullo & Aronson

[57] ABSTRACT

Reusable infant garment such as a diaper, or undergarment, the like configured to have loop means for securement by separate, detachable hook means.

18 Claims, 2 Drawing Sheets

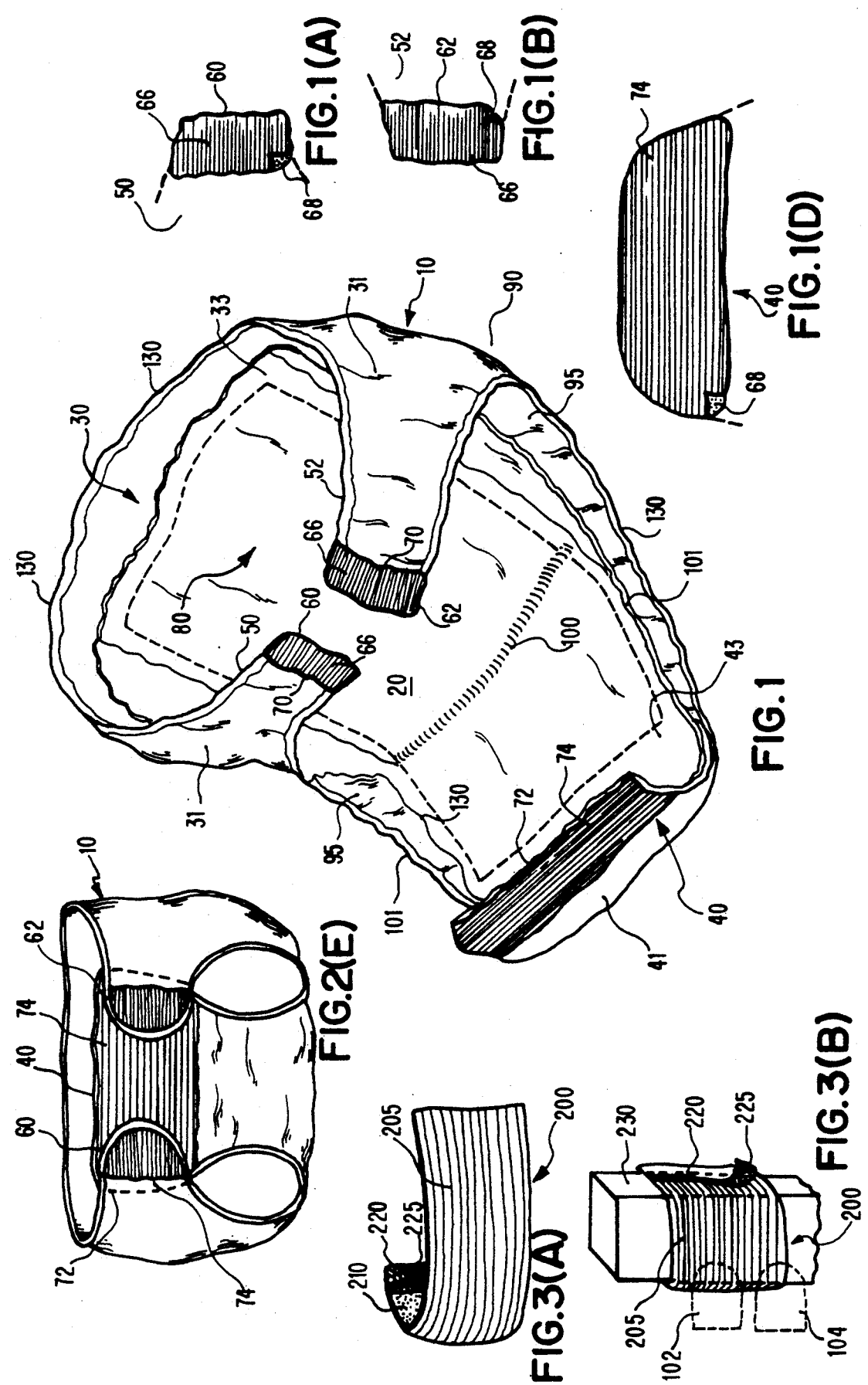

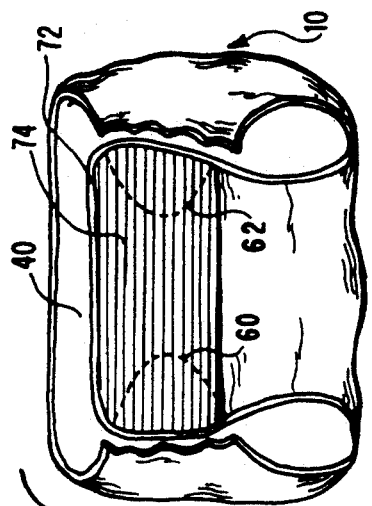
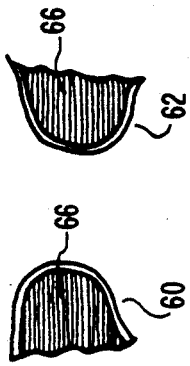
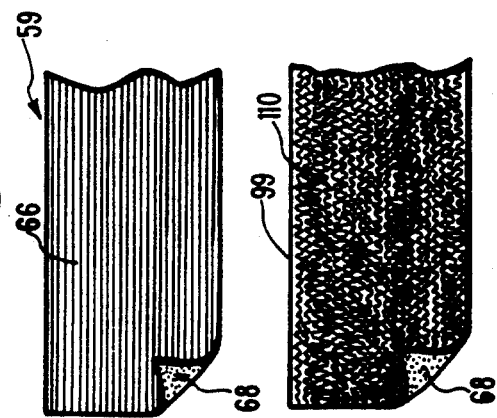
FIG. 1(C)
FIG. 2(C)
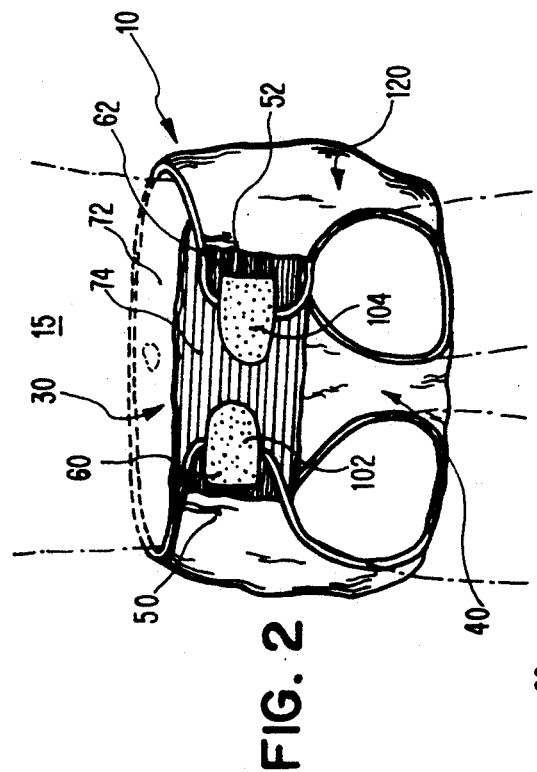
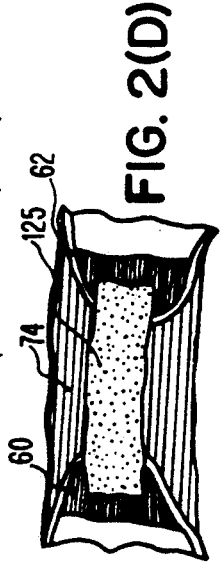
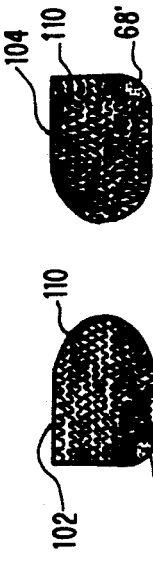
FIG. 2(D)
FIG. 2(B)
FIG. 2(C')
FIG. 2(A)

REUSABLE DIAPER AND THE LIKE

FIELD OF THE INVENTION

This invention relates to diapers, diaper covers and pants-like garments for infants. More particularly the present invention relates to reusable such diapers, diaper covers, garments and the like.

BACKGROUND OF THE INVENTION

Reusable diapers and the like have been made with integral hook and loop members, e.g. the VELCRO TM for securably closing the diaper about an infant.

When the garment is removed from the infant and laundered, in the process of laundering the hook member readily links to other garments being laundered, causing these garments to be damaged and accumulating lint and rovings on the hook and agglomerating the laundered articles into a difficult to separate mass.

Commercially, when washing and/or drying hundreds of pounds of diapers or the like, the agglomeration can result in a "snow balling" effect in which one or more large "balls" of diapers, etc. are created. Such "balls" preclude the proper washing and/or drying and generate excessive vibratory motion which can lead to damaging the washing and/or drying machines.

SUMMARY OF THE INVENTION

The present invention relates to a reusable diaper, diaper cover or infant garment which comprises a cover member which includes a front portion which will, in use, be next to the front of the infant, and a rear portion. Tabs are provided on the sides of the rear portion which will overlie the front portion when the diaper or the like is worn by an infant. The outer surface of the front portion and the outer surfaces of the tabs are provided with loop means, e.g. of the VELCRO TM type, and separate hook means are completely detachable from the garment and are removed completely from the diaper or the like when it is to be washed, thus avoiding the above-noted problems of lint gathering damage and agglomeration of articles during washing.

BRIEF DESCRIPTION OF THE DRAWINGS

FIG. 1 is a perspective view of a reusable diaper or the like in accordance with the present invention;

FIGS. 1(A)-1(D) show individual elements of FIG. 1;

FIG. 2 is a front view of the embodiment of FIG. 1 when arranged for wear on an infant;

FIGS. 2(A)-2(F) show individual elements of FIG. 2; and

FIGS. 3(A), 3(B) show a holder element for closure members of the present invention.

DETAILED DESCRIPTION OF THE PREFERRED EMBODIMENTS

With reference to FIG. 1 a garment or reusable diaper in accordance with the present invention is shown at 10 having a cover member 20 which includes a rear portion 30 with an outer surface 31 and an inner surface 33 and a front portion 40 with an outer surface 41 and an inner surface 43. Rear portion 30 has tabs 50, 52 extending laterally away therefrom, to which are affixed at their end portions respective loop means 60, 62 suitably of the VELCRO TM type shown also in FIGS. 1(A) 1(B). In FIGS. 1(A), 1(B) the loop means 60, 62 are shown each having a loop upper portion 66 and a plain lower surface 68, i.e. having neither loops or hooks. The loop portions 69, 62 can be cut from a commercially available strip shown in FIG. 1(C) at 59. The loop portions 60, 62 can be suitably affixed to the tabs 50, 52 by stitching indicated at 70 or other suitable means or techniques such as adhesives, etc. Front cover portion 40 has across its front peripheral edge 72, spaced away from rear portion 30, a band of loop means 74 of similar material to loop portions 60, 62 shown also in FIG. 1(D). Diaper 10 is suitably configured in a general L-shape 90 and held in this shape by gussets 95 joining and pulling together rear portion 30 and front portion 40 and forming a partial fold 100 as shown in FIG. 1. Optionally, additional absorbent means, such as panel 80 (shown in phantom) may be suitably secured in place within the diaper 10. Elastic edge trim 101 on the free edge of gussets 95 wrap securely and tightly about the infant's legs so as to preclude leakage. Preferably such trim 101 is of greater elasticity than the elastic edge trim 130.

In use, with reference to FIG. 2 the garment or diaper 10, e.g. a reusable diaper is wrapped around infant 15 so that rear portion tabs 50, 52 and loop portions 60, 62 are contiguous to loop portion 74 of front portion 40. Hook portions 102, 104 having hooks 110 shown also in the bottom views of FIGS. 2(A), 2(B), suitably of the VELCRO TM type can be cut from a strip of the type shown at 99 in FIG. 2(C) having a surface with hooks 110 and a plain opposite surface 68 with loop portions 60, 62 of rear portion 30 overlying loop portion 74 of front portion 30, the hook surfaces 110 of hook means 102, 104 are pressed onto loop means 74 to secure the garment 10 to the infant. When removal for washing is required, the hook means 102, 104 are completely separated from the diaper and its completely hook-free periphery 120 can be washed without risk of lint gathering and agglomeration with other garments and damage to other garments or to the washing and/or drying machines. A single strip of hook means 125 as shown in FIG. 2(C) affixed to the outer surface 41 of front portion 40 can be utilized instead of a pair of hook means 60, 62, to join loop means 60 and 62 to loop means 74 as shown in FIG. 2(D). The garment, e.g. a reusable diaper and the like in accordance with the present invention is made of one or more layers of conventional materials such as a soft absorbent material like cotton absorbent flock or velvet, flannel, etc. for the cover means 20, and the outer surface 41 which may be a separate layer of a different material such as an impervious material like rubber or a soft pliable plastic material, etc. In one embodiment a single layer may comprise an absorbent inner side and an impervious outer side. Further in a diaper cover, one impervious layer may be utilized. Suitably stitched substantially about the periphery of the diaper gusset at 130 as shown in FIG. 1 is an elastic edge trim which serves to form fit the garment to the body. As best shown in FIG. 1, the gussets 95 are stitched together with the elastic edge trim 130 to the portions of the diaper structure which form leg openings when in use.

The present invention further includes, in combination, a strip of loop material shown at 200 in FIG. 3(A) with loops indicated at 205, the opposite surface of the strip 200 indicated at 210 is plain except for an end band portion 220 which has hook material 225 affixed to the strip 200 on the side opposite the loop material. The strip 200 is suitably wrapped around a member 230, which can be part of a baby changing table, crib, chair or other household item, so that the end band portion 220 overlies loop material of strip 200 as shown in FIG. 31(B). In this position strip 200 wraps around and engages member 230 tightly so as to remain stationary and in place so that same can be used as a convenient holder for a plurality of hook means 102, 104, which are used in securing the reusable diaper or other garment as shown in FIG. 2. Optionally, the loop material 200 may have an adhesive backing for convenient mounting and securement. In this connection in the loop material 200 can be secured to the member 230 by any suitable means, such as nails, staples, tacks, screws adhesives or cement, etc.

While the invention is disclosed and more particularly described with the presently preferred embodiment, it is not intended that the invention be limited to the described embodiment. It will be obvious to those skilled in the art that modifications may be made without departing from the scope and spirit of the invention. Thus it is intended that the appended claims cover all equivalent variations as may be subsequently contemplated.

What is claimed is:

1. A reusable infant garment comprising a cover member having a panel with an impervious front portion, an absorbent rear portion, and a periphery including an inner surface and an outer surface;

first and second tab means affixed to the rear portion and extending away therefrom, each tab means having an outer and inner surface with at least portions of the inner surface of each tab means being adapted to abut the outer surface of the front portion of the cover member;

first loop means affixed to the outer surface of the first tab means;

second loop means affixed to the outer surface of the second tab means;

third loop means affixed to the outer surface of the front portion of the cover member; and at least one separate detachable hook coupling means for detachably engaging said first, second, and third loop means;

whereby when the cover member is folded so that the first and second tab means are opposite each other and contiguous to the third loop means, said separate detachable hook coupling means is applied to the first, second and third loop means to fasten said first tab means and said second tab means of the rear portion to the front portion of said cover member, and said hook coupling means being removable so as to facilitate washing of a plurality of said reusable infant garments.

2. The reusable infant garment in accordance with claim 1, wherein said front portion of the cover member has an edge portion spaced away from said first and second tab means and said third loop means is a strip of loop means affixed to the outer surface of the front portion of the cover member adjacent said edge portion.

3. The reusable infant garment in accordance with claim 1, wherein said separate hook means are a pair of hook means comprising two similarly size separate tab shaped hook means for respectively detachably joining the first loop means and said second loop means to said third loop means.

4. The reusable infant garment in accordance with claim 1, wherein said at least a separate hook coupling means is a rectangularly-shaped strip of hook means for detachably joining both the first loop means and the second loop means to the third loop means.

5. The reusable garment in accordance with claim 1, wherein the periphery of the cover member is free of any hook means.

6. The reusable garment in accordance with claim 1, wherein said front and rear portion of said panel are held in a generally L-shaped configuration by gusset means bridging said front and rear portions.

7. The reusable infant garment in accordance with claim 1, which further includes a strip having a first side and a second side, the first side having affixed thereto loop means substantially covering said first side and the second side having a relatively small portion of hook material affixed thereto adjacent an end of said strip, said strip being wrappable around a post member and securable thereto upon engagement of said hook material portion with underlying loop material, whereby said loop means of the strip surround said post and can detachably engage the separate hook coupling means.

8. The reusable garment in accordance with claim 1, wherein said front portion is of fluid impervious material and said rear portion is of a substantial absorbent material.

9. The reusable garment in accordance with claim 8, wherein said materials comprise a single layer.

10. The reusable garment in accordance with claim 8, wherein said front portion is a single fluid impervious layer facing said rear portion.

11. The reusable garment in accordance with claim 1, further including a separate strip of loop material secured to a member for detachably engaging the separate hook coupling means when not in use with said diaper.

12. The reusable garment in accordance with claim 1, further including gusset means joining together said front and rear portions of said garment.

13. The reusable garment in accordance with claim 12, wherein said gusset means comprises a pair of gussets having elastic edges for precluding leakage when said garment is in use.

14. The reusable garment in accordance with claim 13, further including an elastic edge substantially about the periphery of said garment.

15. The reusable garment in accordance with claim 14, wherein said elastic edges of said gussets are of greater elasticity than said elastic edge of said garment.

16. The reusable garment in accordance with claim 1, further including an additional absorbent layer of material between said front and rear portions of said garment.

17. In combination a post member and a reusable infant garment comprising a cover member having a front portion, and a rear portion, a periphery including an inner surface and an outer surface;

first and second tab means affixed to the rear portion and extending away therefrom, each tab means having an outer and inner surface with at least portions of the inner surface of each tab means being adapted to abut the outer surface of the front portion of the cover member;

first loop means affixed to the outer surface of the first tab means;

second loop means affixed to the outer surface of the second tab means;

third loop means affixed to the outer surface of the front portion of the cover member;

at least one separate hook coupling means for detachably engaging together said first, second and third loop means; and separable compatible strip means having a first side and a second side, the first side having affixed thereto a fourth loop means substantially covering said first side and the second side having a relatively small portion of hook material affixed thereto adjacent an end of said compatible strip means, said separable compatible strip means being wrappable around said post member and securable thereto upon engagement of said hook material portion with underlying loop material, whereby said loop means of said strip means surround said post member and can detachably engage the separate hook coupling means.

18. In combination a post member and a reusable infant garment, said garment comprising a cover member having a front portion, a rear portion, and a periphery including an inner surface and an outer surface;

first and second tab means affixed to the rear portion and extending away therefrom, each tab means having an outer and inner surface with at least portions of the inner surface of each tab means being adapted to abut the outer surface of the front portion of the cover member;

first loop means affixed to the outer surface of the first tab means;

second loop means affixed to the outer surface of the second tab means;

third loop means affixed to the outer surface of the front portion of the cover member;

whereby when the cover member is folded about an infant the first and second tab means are opposite each other and contiguous to the third loop means;

at least one separate hook coupling means detachably engaging together said first, second and third loop means when in use with said reusable infant garment; and a separate compatible strip of loop material adapted to be secured about said post member for detachably engaging the separate hook coupling means when not in use with said reusable infant garment.

* * * * *